United States Patent
Chaniotakis et al.

[11] Patent Number: 5,840,168
[45] Date of Patent: Nov. 24, 1998

[54] SOLID CONTACT ION-SELECTIVE ELECTRODE

[75] Inventors: Nikolas A. Chaniotakis, Iraklion, Greece; Steven J. West, Hull, Mass.

[73] Assignee: Orion Research, Inc., Beverly, Mass.

[21] Appl. No.: 490,935

[22] Filed: Jun. 16, 1995

[51] Int. Cl.$^6$ .................................................. G01N 27/20
[52] U.S. Cl. .......................... 204/416; 204/418; 204/419; 204/435; 204/294; 422/56; 422/82.03
[58] Field of Search ..................................... 204/403, 416, 204/418, 435, 419, 294; 422/56, 82.03

[56] References Cited

U.S. PATENT DOCUMENTS

| | | | |
|---|---|---|---|
| 4,670,218 | 6/1987 | Gantzer et al. | 422/56 |
| 5,160,419 | 11/1992 | Kageyama et al. | 204/418 |

OTHER PUBLICATIONS

Stevens, A., et al. "Coated–wire cadium ion–selectice electrode based on the Bidentate Neutral Carrier 4,4'–di(5–nonyl)–2,2' Bipyridine", *Analytical Chemica Acta*, 248:315–321 (1991).

Cattrall, R.W., et al., "Coated Wire Ion Selective Electrodes", *Analytical Chemistry*, 43:13 Nov. 1971.

Hansen, Ruzicka, et al., "Selectrode—The Universal Ion–Selective Electrode", *Analytica Chemica Acta*, 67:15–178 (1973).

Durselen, L. et al., "New Solid–State Contract for Ion–Selective Liquid Membrane Electrodes", *Chimia*, 44:214–215 (1990).

*Primary Examiner*—Bruce F. Bell
*Attorney, Agent, or Firm*—Ernest V. Linek; Dike, Bronstein, Roberts & Cushman, LLP

[57] ABSTRACT

A new substrate for the construction of solid internal contact ion-selective electrode comprising a conductive and porous carbon matrix is described. The well-defined (i.e., fixed) interfacial potential between the organic electroactive phase and the internal reference element, coupled with the electrode's very slow change from water activity at the internal reference element, supports the well-behaved and reproducible electrode operation. Solid contact sensors for two different ions were constructed, and their potentiometric behavior was compared with their symmetric counterparts. The potentiometric response was monitored over a period of one month with excellent results for drift, base line stability, response time, selectivity, and detection limit.

7 Claims, 6 Drawing Sheets

SOLID CONTACT ION-SELECTIVE ELECTRODE

BACKGROUND OF THE INVENTION

The use of Ion Selective Electrodes (ISEs) in the analysis and monitoring of charged as well as neutral species and gases has been expanding for a number of years. See for example, Ruzicka J. et al., *Anal. Chim. Acta,* 62, 15–28 (1972); Ruzicka J. et al., *Anal. Chim. Acta,* 67, 155–78 (1973); Hulanicki A. et al., *Analust,* 107, 1356–62 (1982); Stevens C. A. et al., *Anal Chim. Acta,* 248, 315–21 (1991).

For routine analysis, the symmetric configuration in which the sensing membrane comes in direct contact with two aqueous solutions, the internal with fixed ion activity and the external with the ion activity to be measured, has been used with great success. Even though the symmetric ISEs have found a wide range of applications they still have certain inherent limitations. For instance, they are mechanically complicated, and thus difficult to manufacture in small size; the internal solution increases the system impedance, and finally, due to internal compartment, they cannot withstand high pressures. See for example, Selig W., *Anal Letters,* 15(A3), 309–29 (1982); Cattral R. W. et al., *Ion Selective Electrode Rev.,* 6, 125–71 (1984); Nikolsky B. P. et al., *Ion Selective Electrode Rev.,* 7, 3–39 (1985); Cunningham L. et al., *Analytica Chimica Acta,* 180, 271–79 (1986).

Solid contact ion-selective electrodes (SC-ISEs) refer to a type of ISE in which the internal reference electrode contains no aqueous solution. See for example, Selig, supra; Nikolsky et al., supra; Durselen, L. et al., *Chimica,* 44, 214–15 (1990); and Ruzicka J. et al., *Anal. Chim. Acta,* 53, 1–12 (1971). In SCEs there is a direct contact between the electroactive organic phase and the internal reference element. Examples of this sensor design include the coated-wire electrodes (CWE) (see for example, Cattral et al., supra; Cunningham et al., supra;, James H. et al., *Anal. Chem.,* 44, 856–60 (1972) and Khalil M. M., *Analytical Letters,* 26(1), 55–71 (1993)); hybrid sensors and the ion-selective field effect transistors (see for example, Harrison J.D. et al., *Electrochem. Soc.: Electrochemical Science and Technology,* 2473–78 (1988); Winquist F. et al., *Biosensors (Practical Approach Series),* Oxford 1990; Chapter 7.

Since the introduction of the first graphite rod ISE (Ruzicka J. et al., *Anal. Chim Acta,* 53, 1–12 (1971)) and the first coated wire electrode (Cattrall, R. W. et al., *Anal. Chem.,* 43, 1905–06 (1971)), considerable work has been devoted to the construction of ISEs with no internal solutions. Such an electrode will have certain advantages such as its small size, lower cost of production, and ability to operate in environments where the symmetric ISEs can not. The key issue in the design of these sensors has been defining the interface between the organic electroactive membrane and the internal reference element in order to obtain potentials which are stable, are not dependent on redox species in the samples nor are affected by water itself. The failure so far to precisely define this interfacial potential has limited the success of the SC-ISEs.

SUMMARY OF THE INVENTION

The SC-ISEs of the present invention are very simple to make and easy to care for. They can be used in the same way as the symmetric ISEs while at the same time having certain advantages thereover. Their cross-sectional size can vary considerably (e.g., from several centimeters (cm) to less than one millimeter (1 mm)) depending on the application requirements, while the elimination of the internal compartment will allow their operation in high pressures. This is especially important because the electrodes of the present invention contain no aqueous solution or air bubbles, thereby making them suitable for modern planar and/or mass production manufacturing techniques. This lack of an aqueous solution or air bubbles also makes the present electrodes suitable for miniaturization. This lack of an aqueous solution or air bubbles also enables the electrodes of the present invention to be used in samples which are under high pressure, such as occur in the deep ocean.

Thus, one aspect of the present invention is directed to a substrate useful for the construction of solid internal contact ion-selective electrodes comprising a conductive and porous carbon matrix, whereby the interfacial potential between the organic phase containing selective ion carriers or hosts and the internal reference element of the electrode is precisely defined (or fixed as discussed below). Preferably, the interfacial potential is fixed by selection of an appropriate metal (M) and metal salt (MX) and the presence of an aqueous layer becomes both unnecessary and undesirable.

For example, in electrodes of the present invention, the metal (M) may advantageously be selected from silver, copper, lead, or mercury, but need not be limited to these metals, and the anion (X) of the salt may advantageously be selected from chloride, bromide, iodide, or perchlorate, but again, need not be limited to these anions.

In one embodiment of the present invention, the porous carbon substrate is advantageously impregnated with an organic phase containing ion carriers and hosts and the hydrophobic nature of this phase inhibits penetration or permeation of water from an aqueous sample solution external to the electrode eventually contacting the reference metal and salt. The purpose of preventing such penetration is to prevent interference with the precisely defined interfacial potential. In one preferred embodiment, the organic phase contains or comprises the solvent bis(2-ethylhexyl)sebacate (DOS) and the polymer poly(vinly chloride) (PVC) but it need not be limited to these materials. In another preferred embodiment, the organic phase contains or comprises the solvent ortho-nitrophenyl octyl ether (o-NPOE) although other solvents known to those skilled in this art may likewise be employed.

In one embodiment of the present invention, the ion carriers nickel-phenanthroline or tridodecylmethylammonium nitrate, dissolved in the organic phase, permits sensing of the ion nitrate; but the skilled artisan will readily recognize that other well known ion carriers will be used for the sensing of other anions. In another embodiment, the ion carrier valinomycin dissolved in the organic phase permits sensing of the ion potassium. Again, the use of other known ion carriers for the sensing of other cations is part of this invention as well.

In the present specification, SC-ISEs for one anion, $NO_3^-$, and one cation, $K^+$, are presented in detail, but the skilled artisan will appreciate that the same or similar configurations can be used for the construction of SC-ISEs for many other ionic species, as long as the theoretical requirements described in detail below are fulfilled. Thus, this invention is not to be construed as being limited to the two preferred embodiments being described.

DETAILED DESCRIPTION OF THE PREFERRED EMBODIMENTS

The symmetrical configuration of an ISE contains the internal and the external interface, which under most circumstances are identical:

Internal Interface $\delta_1$   External $\delta_2$

In this arrangement, the phase boundary potentials $\delta_1$ and $\delta_2$ are well defined, and assumed not to influence one another. In order for an ISE to have stable and reversible potential, the following three requirements need to be fulfilled regarding its interfaces:
  a) There should be a reversible and stable process of electronic into ionic conductivity and vise-versa at the internal reference electrode interface.
  b) The exchange currents taking place at the reference elements which depend on the electrode reactions should be very high.
  c) The internal contact must be isolated and well protected from any side reactions.

See, Nikolsky, B. P. et al., *Ion Selectrive Electrode Review*, Vol. 7, pp. 3–39 (1985).

When the reference element of an ISE is replaced by a redox system (Pt, Au) to form a solid internal contact electrode, the following system is obtained:

Internal Interface   External Interface

It can be seen that the internal boundary potential cannot be precisely controlled due to two basic reasons:
  a) The potential of the metal surface depends on the redox condition of the membrane, which in turn is dependent on the chemical species present at that interface.
  b) Since the charge conduction across the ISE membranes is usually carried out by ions, there is a mismatch of ionic to electronic charge conduction at the internal reference element where only electron conduction can take place.

The replacement of the noble metal (Pt) with a Ag/AgCl or Cu contacts has recently found considerable use, but still its behavior is not well documented and the interface potentials generated are still not very stable. See for example, Durselen, L. et al., *Chimica,* 44, 214–15 (1990) and Fjeldly, T. A. et al., *J. Electrochem. Soc.,* 126, 793 (1979).

In the case of Ag/AgCl, the activity of the anion X will determine the potential of the M/MX couple. The amount of water that penetrates the membrane becomes the major factor influencing this potential, since it usually decreases the activity of the ions present. One approach in solving this problem is to deposit a solid electrolyte (e.g., KCl) or an aqueous gel, which contains a certain activity of a primary ion, directly onto the Ag/AgCl or Cu reference elements. Such an approach generates a symmetric ISE, but the osmotic pressure of water inside the membrane cannot be controlled leading to continuous changes in ion activities. The water accumulation will result in the "blowing" of the ISE membrane and finally its separation from the metal support.

The SC-ISEs described in this specification are able to overcome these problems, and offer an alternative to the construction of non-symmetrical liquid membrane potentiometric sensors. A schematic diagram of the system presented here is as follows:

| Lipophilic Organic Phase |

Figure 1:
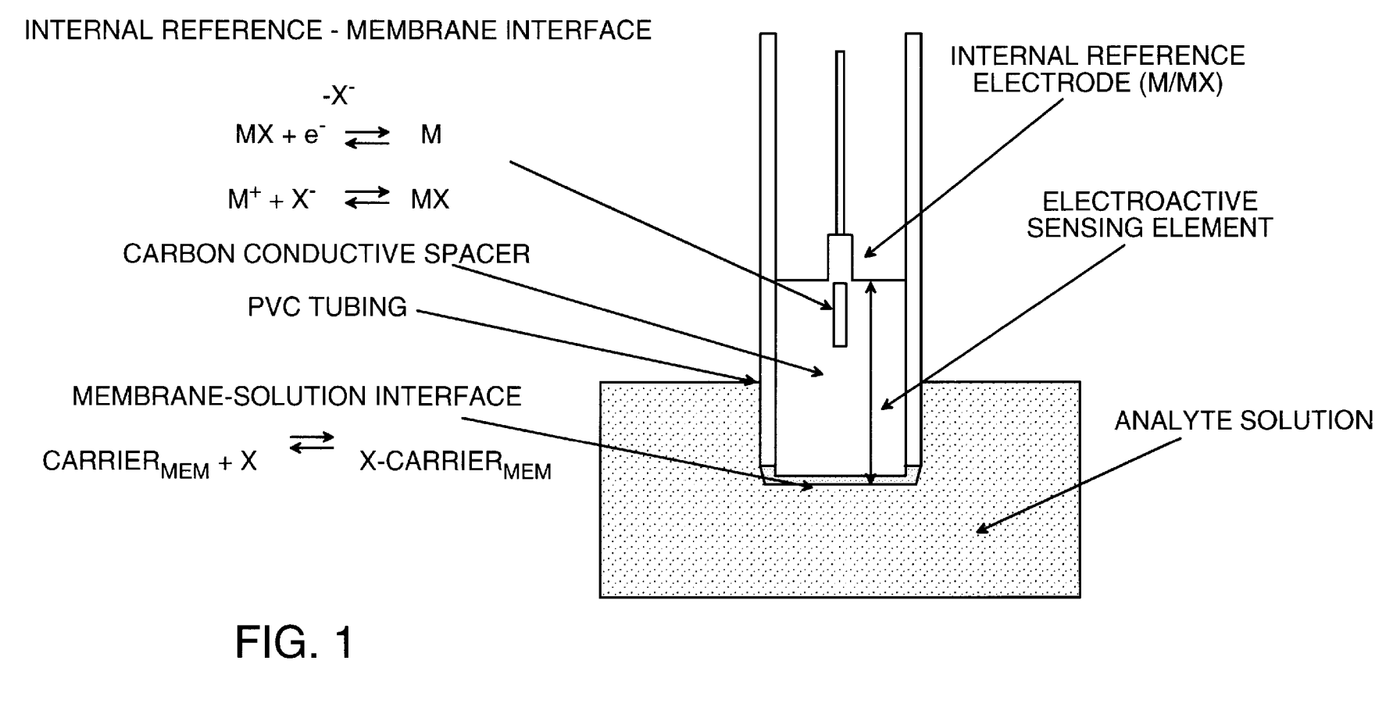
FIG. 1 is a schematic diagram of a solid contact electrode (SC-ISE) of the present invention.

The potentiometric half-cell considered here consists of two parts, the internal solid reference and the electroactive sensing element (FIG. 1).

In order for the internal reference system to be well defined, it has to have the previously described characteristics, i.e., it must have a stable potential, fast electronic to ionic conductivity-process and isolation from side reactions.

It is known that if the concentration of a salt MR or RX in the membrane organic phase is high enough, the condition that $a_m$ or $a_x$ is much larger than $\sqrt{K_{MX}}$ is fulfilled (see, Nikolsky et al., supra) where $K_{MX}$ is the solubility product of the MX in the membrane phase. Under this condition, the organic solution will possess high buffering toward the activities of the $M^+$ and $X^-$ ions, thus the M/MX internal reference-contact element (such as that of Ag/AgCl) will process a stable potential. The possibility to use different metal reference elements (e.g., Cu, Pb, Hg) as well as salts (RX where $X=Cl^-, Br^-, I^-, ClO_4^-$ or MR where $M=K^+, Ag^+, Cu^{2+}$) cover a wide range of potentiometric systems.

The present SC-ISE has been designed based on the concept that the amount of a salt in the organic electroactive phase is large in order to stabilize the interface potential as mentioned above, and thus satisfies the internal reference stability requirement. In the case of the $K^+$ -selective SC-ISE, the high activity of $Cl^-$ in the membrane phases is obtained by the use of a layer of solid KCl in contact with the organic phase (see, FIG. 1); see also Iglehart, M. L. et al., *Anal. Chem.,* 60, 290–95 (1988) and Cammann, K., *Anal. Chem.,* 50, 936–40 (1978).

The same holds true in the case of the $NO_3^-$ selective SC-ISE. It should also be mentioned that the presence of the ion carriers will aid in the dissolution of the salt in the membrane phase.

The electronic conductivity requirement is satisfied when the following reversible fast equilibrium exists:

$$MX + e^- \leftrightarrows M^\circ + X^- \quad (1)$$

where M is the metal conductor (i.e., Ag), and MX is the metal salt such as AgCl.

The ionic to electronic conductivity will be satisfied only in the case where the membrane components (carrier or any other membrane additive) allow for one of the following equilibria to exist:

$$M^{+n} + \text{Carrier}_{(mem)} \leftrightarrows M^{+n}\text{-Carrier}_{(mem)} \quad (2)$$

$$X^{-n} + \text{Carrier}_{(mem)} \leftrightarrows X^{-n}\text{-Carrier}_{(mem)} \quad (3)$$

This equilibria will offer the required buffering capacity in the system to support the equilibrium shown in equation (1). It is clear that when either a complexing carrier such as valinomycin or Ni-Phenanthroline, or an ion exchanger such as TDMACl or K-TPhB which has selectivity for either the anion of the metal salt that takes part in the reference couple ($Cl^-$ in the case of AgCl), or a counterion of $Cl^-$ (such as $K^+$ in the case of KCl), valinomycin will complex $K^+$ according to equation (2) yielding equation (4):

$$KCl_s + \text{Valinomycin}_{(mem)} \leftrightarrows K^+ \text{-Valinomycin}_{(mem)} + Cl^- \quad (4)$$

Figure 4:
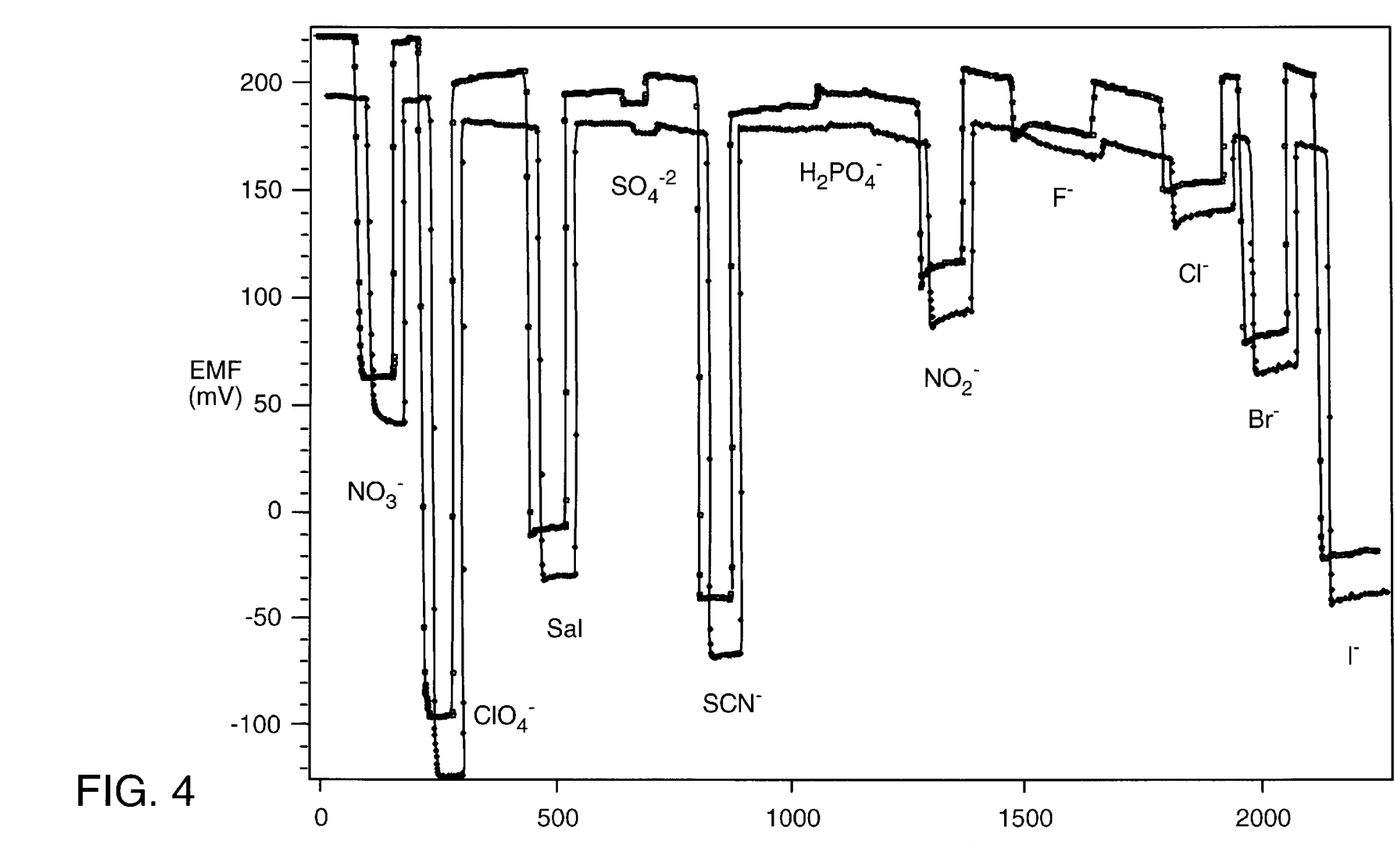
FIG. 4 is a graphic representation of the potentiometric selectivity of $NO_3^-$ electrodes; SC-ISEs (diamonds) and commercial symmetric electrodes (circles). The data for the SC-ISE were offset for clarity.

At the same time, and in the case of the $NO_3^-$ selective SC-ISE, the Ni-Phenanthroline exchanger possesses affinity for $Cl^-$ (see $NO_3^-$ selectivity FIG. 4), thus equation (3) is satisfied yielding equation (5):

$$KCl_s + \text{Ni-Phen}_{(mem)} \leftrightarrows Cl^- \text{-Ni-Phen}_{(mem)} + K^+ \quad (5)$$

The third requirement, isolation of the internal reference element from any side reactions, can be achieved if water from the aqueous solution is not allowed to reach the internal reference element, and thus change the activities of the electroactive species. Since the presence of just the polymeric membrane is not adequate to prevent the transport of water to the reference contact, it is thought that the introduction of a very lipophilic and conductive spacer between these two phases will suffice, at least for a certain time period. The spacer used for the construction of the electrodes presented here has very high conductivity (25 ohms-centimeters) allowing for remote placing of the internal reference element, while its impregnation with the organic cocktail (i.e., plasticizer, carrier, and additives) gives the required high lipophilicity. The potential stability observed with these SC-ISEs confirms this postulation (see below).

EXAMPLES

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

The experiments performed with this type of electrode were designed in order to compare directly the potentiometric behavior of the SC-ISE with that of the commercially available symmetric ISEs. In particular, the potentiometric stability over time, response time, base line return, selectivity, and detection limit were examined.

Apparatus and Reagents:

Valinomycin used in potassium electrodes was purchased from Sigma Chemical Co. (St. Louis, USA). Ni-Phenanthroline in o-NPOE used as a $NO_3^-$ carrier-plasticizer cocktail was obtained from ATI ORION Research (Boston, USA). Bis(2-ethylhexyl) sebacate (DOS) and high-molecular-weight PVC used in the membrane cocktail were made by Fluka. The carbon rods were made of compressed charcoal (No 192/1, Austria). Masterflex® 6409-16 TYGON® tube, manufactured by NORTON was used in the electrode construction. All other chemicals were of reagent grade. Tetrahydrofuran (THF) was freshly distilled before use. Symmetric commercial electrodes, for comparison, were obtained from ATI ORION Research, Boston USA: Model 93-07 Nitrate and 93-19 Potassium. De-ionized, 18 MΩ water was used to prepare all aqueous solutions.

Electrode Construction:

Round carbon rods with 0.55 cm diameter and 1.0 cm length were used for the construction of the electrode sensor element. A hole of the same diameter as that of the reference silver wire (0.05 cm diameter and 0.2 cm depth) is drilled on the one side of the carbon rod. The anodized silver wire is then placed tightly into the hole of the carbon rod, and soldered to shielded wire. This assembly is placed into a Masterflex® 6409-16 TYGON® tubing, 15 cm long, with the carbon rod extended 0.05 cm outside the tubing, and subsequently dipped into the liquid carrier cocktail. Capillary action enables the carbon rod to absorb the carrier cocktail in a few hours, and be completely saturated by it. Finally, the exposed side of the electrode and the side of the TYGON® tubing is covered with PVC-based membrane cocktail, and is allowed to evaporate overnight, forming a 0.01 cm thick membrane. See FIG. 1.

EMF Measurements:

All EMF measurements were performed at 25° C.±1° controlled with an Edmund Büller, D-7400 water heater-circulator in double wall beakers, using a XENON CI-317 8 channel Electrochemical Measuring System, (XENON Halanthri, Athens Greece) with input impedance >$10^{13}$ ohms, versus an ATI Orion Research 900200 double junction reference electrode. All other measurement procedures were obtained from the Orion Model 93-07 Nitrate Electrode and Model 93-19 Potassium Electrode Instruction Manuals; see, ATI Orion Research Incorporated, Model 93-07, *Nitrate Electrode Instruction Manual*, 1991 and Model 93-19, *Potassium Electrode Instruction Manual*, 1991.

The long term stability measurements were performed in a solution of 0.01M of sodium nitrate or potassium chloride respectively containing also the ionic strength adjustors suggested in the Orion Manuals. The electrodes were tested and stored in the appropriate solution until the next measurement at which time the test solution was replaced with a fresh one. The selectivity measurements were performed by one addition of 2.50 mL of 0.10M of the appropriate salt solution into 25.00 mL of the ionic strength adjustor, bringing the final concentration of the salt to 0.0153M. The calibration curves were obtained by serial addition of concentrated sample. The data were collected in a DALE 486 DX personal computer via a ADC-16, 16-bit Keithley A/D converter board, and displayed using a program written in BASIC. The measurements were not corrected for junction potentials or activity coefficients. No pretreatment was performed on any of the electrodes before use.

Figure 2:
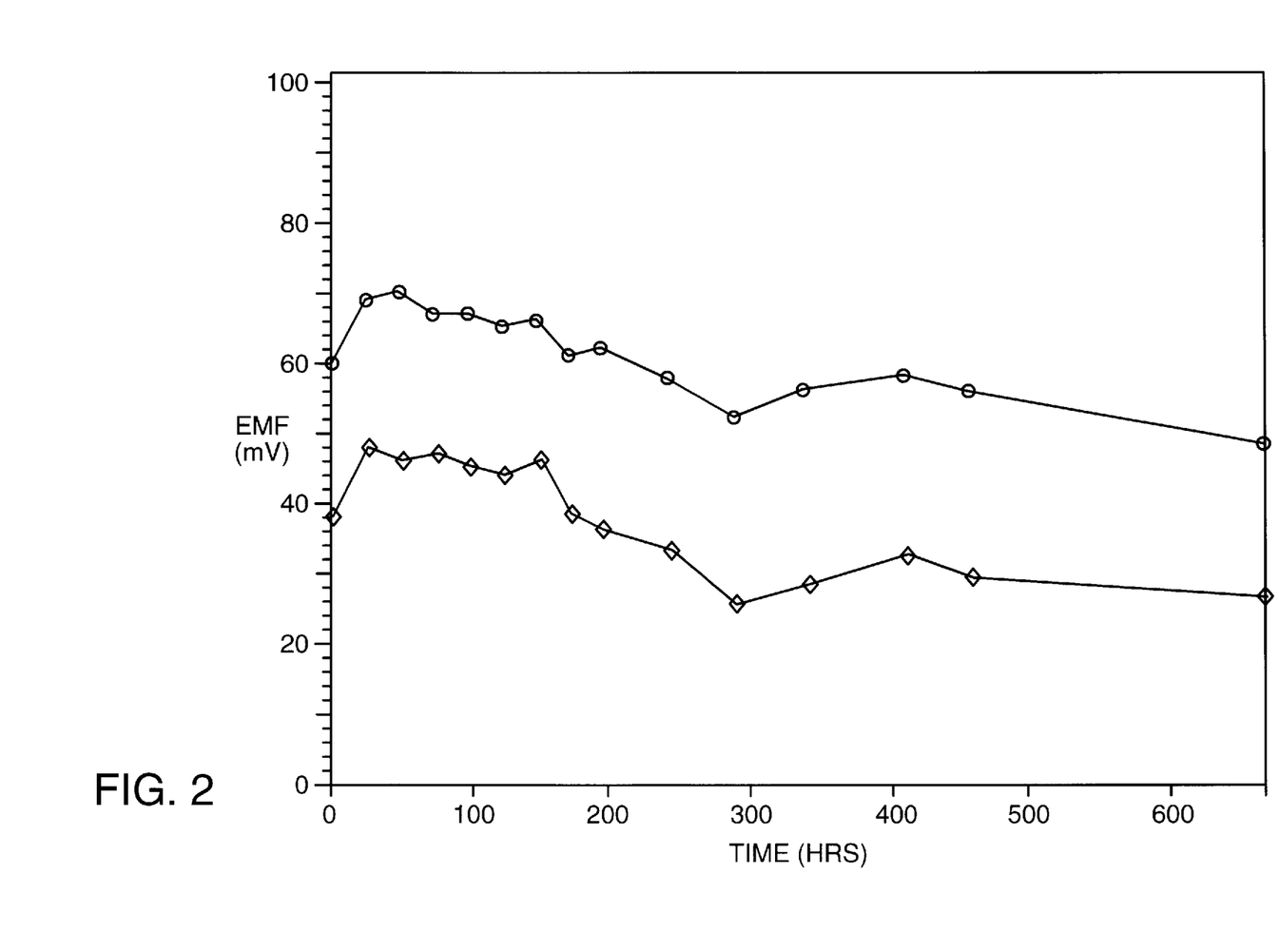
FIG. 2 is a graphic representation of the potentiometric stability of $NO_3^-$ electrodes over 30 days, for both SC-ISEs (diamonds) and commercial symmetric electrodes (circles).

(A) Potential stability of the SC-ISEs over time:

The major drawback of SC-ISEs has been their large potential drift, probably due to the large water uptake. In order to determine the stability of the SC-ISE systems over a one-month period of continuous testing, their potential was monitored. FIG. 2 shows the EMF stability of the $NO_3^-$ electrodes under investigation. The potential drift of the solid contact electrode is comparable to the symmetric commercial ISE. The small variations of the potentials between measurements observed with both electrodes could be due to drifts of the measuring systems, such as that of the reference potential and small temperature fluctuations. This stability indicates that the internal reference element remains isolated from any water transport over at least one month of continuous examination, and that the electroactive membrane remains intact, and fully operational (see also calibration results). The same holds in the case of the $K^+$ electrode (results not shown).

Figure 3:
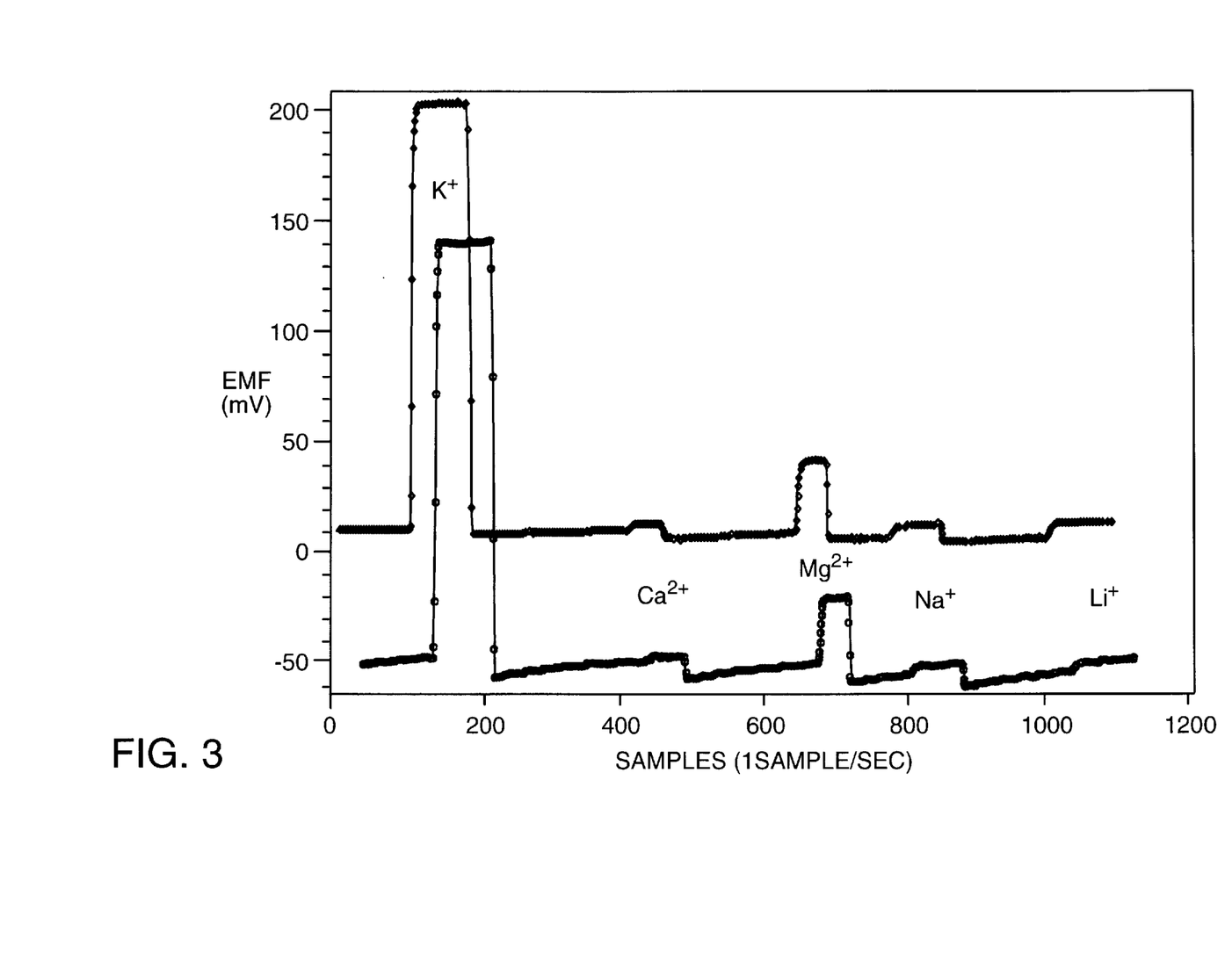
FIG. 3 is a graphic representation of the first day selectivity of $K^+$ electrodes; SC-ISEs (diamonds) and commercial symmetric electrodes (circles). The data for the commercial electrode were offset for clarity.

(B) Selectivity:

The selectivities of the electrodes were examined in order to determine the chemical stability of the SC-ISE systems, and the possible influence of the carbon rod. Even though the SC-ISE $K^+$ selective membrane did not contain any lipophilic additives, the obtained selectivities are comparable. FIGS. 3 and 4 show the selectivities of the SC-ISEs and the commercial ISEs. The results presented here were obtained the first day of testing but the same holds even after a period of 30 days.

Figure 5:
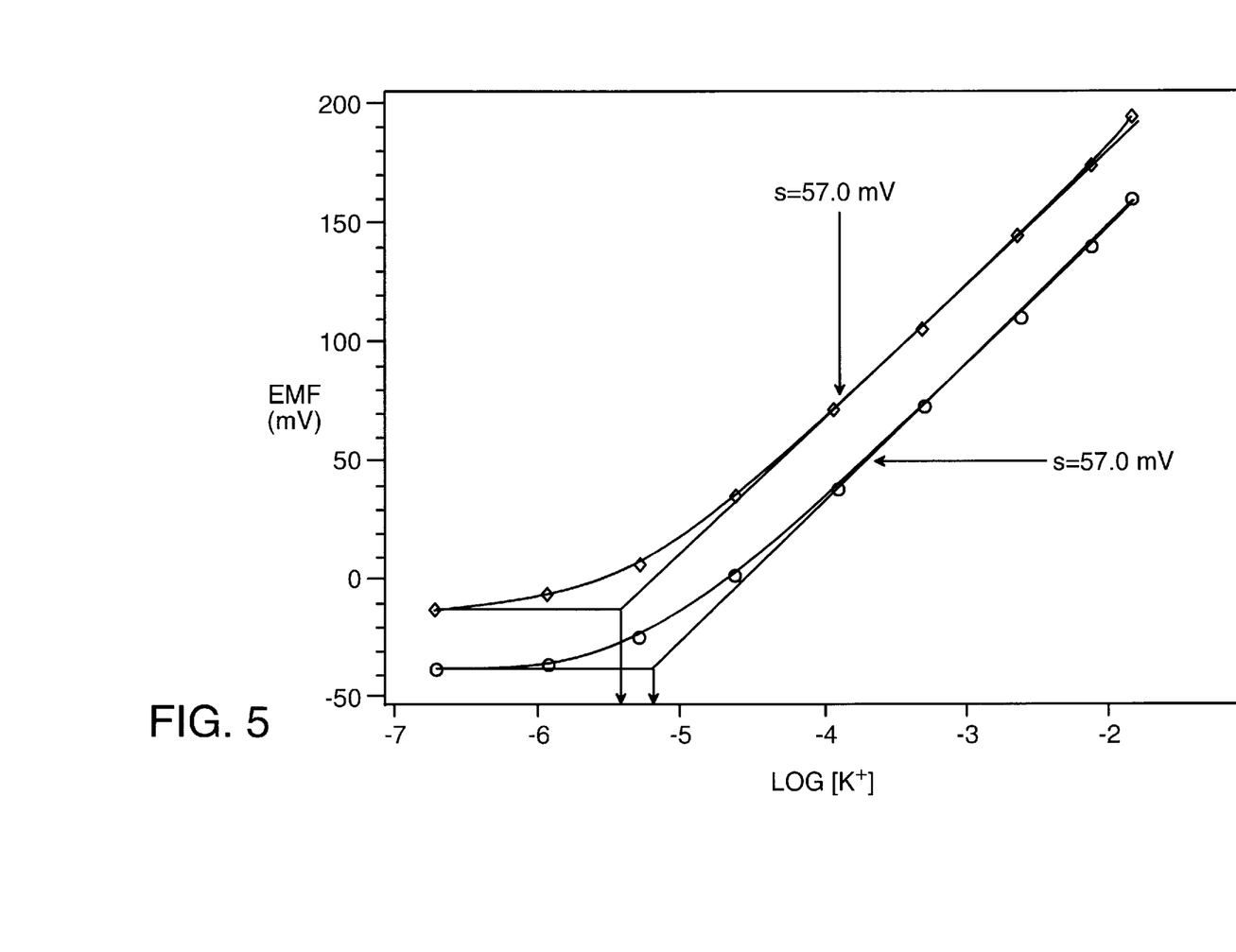
FIG. 5 illustrates the calibration curves of $K^+$ electrodes; SC-ISEs (diamonds) and commercial symmetric electrodes (circles). The data for the electrodes were offset for clarity.
Figure 6:
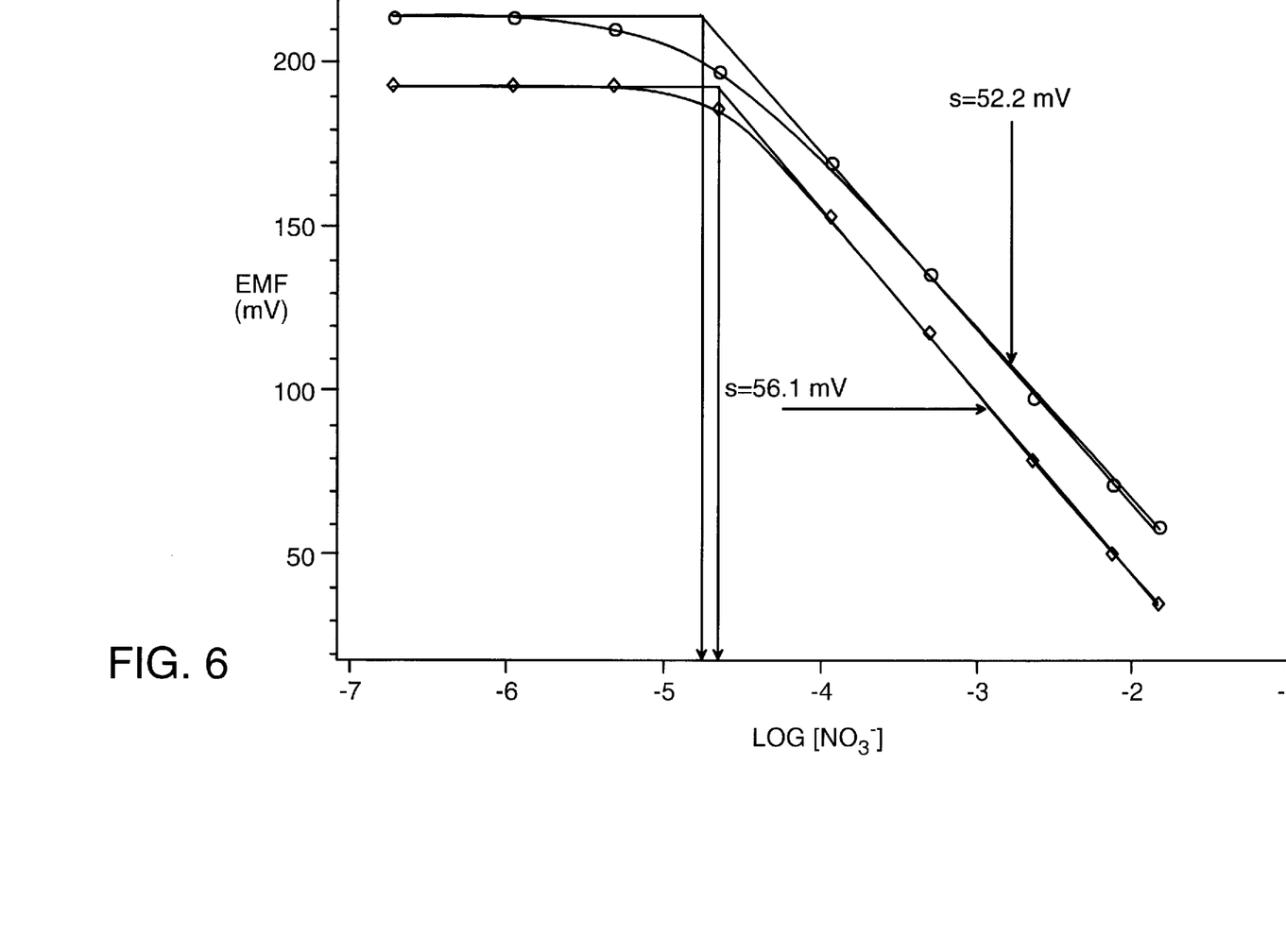
FIG. 6 illustrates the calibration curves of $NO_3^-$ electrodes; SC-ISEs (diamonds) and commercial symmetric electrodes (circles).

(C) Calibration curve and detection limits:

The results from the calibration curve of the electrodes provide information on the slope as well as the detection limit of the systems. FIG. 5 and 6 shows the calibration curves for $K^+$ and $NO_3^-$ of the SC-ISE and commercial symmetric electrodes, while the slopes and detection limits are also indicated according. Even though the slope of the $K^+$ electrodes were identical at the end of the one month test period, that of the $NO_3^-$ was a little lower (5 to 10%) for both the SC-ISE and the commercial (ORION) electrodes (data not shown).

(D) Response time and base line return:

The response time of the SC-ISEs is at least as fast as that of the symmetrical type, s can be seen from FIG. 3 and 4. The base line return is also very fast, and reproducible in all electrodes examined.

(E) Further Improvements:

Investigations continue for the complete evaluation of the SC-ISE systems presented here. The possibility of the elimination of the polymeric membrane is being examined. The use of this electrode system in conjunction with a series of existing ion carriers, additives, and lipophilic metal salts is under way. At the same time, the possibilities for use of these sensors in deep sea research, in a micro sensor array, as well as substrates from biosensors are under investigation. All of these improvements are presently believed to be possible, given the current state of the inventors understanding of this system.

The use of highly conductive porous carbon rods enables the construction of a new type of SC-ISE with stable and reproducible potential characteristics over both short and long time periods. From the results obtained during the one month investigation of the SC-ISEs, it is clear that the new electrode configuration presented here is at least as good as the symmetric state of the art ISEs. The elimination of the potential drift due to the stable internal reference electrode, coupled with the possibility of the use of such systems in environments where symmetrical ISEs are not able to operate, may lead to their application in many new ares of ion analysis.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A solid contact ion-selective electrode comprising a substrate comprising a conductive and porous carbon matrix, wherein the interfacial potential of said electrode is fixed by the presence of a metal M and metal salt MX in said substrate, and wherein the presence of an aqueous layer is substantially eliminated, so that the electrode contains essentially no aqueous solution or air bubbles.

2. An electrode of claim 1, wherein the metal M is selected from the group consisting of silver, copper, lead, and mercury; and wherein the anion X of the salt is selected from the group consisting of chloride, bromide, iodide, and perchlorate.

3. An electrode of claim 1 or 2, wherein the porous carbon substrate further comprises an organic phase containing ion carriers and hosts and wherein the hydrophobic nature of this organic phase inhibits penetration or permeation of water from an aqueous sample solution external to the electrode.

4. An electrode of claim 3, wherein the organic phase comprises the solvent bis(2-ethylhexyl)sebacate and the polymer poly(vinly chloride).

5. An electrode of claim 3, wherein the organic phase comprises the solvent ortho-nitrophenyl octyl ether.

6. An electrode of claim 3, wherein the ion carrier in the organic phase is selected from the group consisting of nickel-phenanthroline and tridodecylmethylammonium nitrate, thereby permitting the sensing of the ion nitrate.

7. An electrode of claim 3, wherein the ion carrier in the organic phase is valinomycin, thereby permitting the sensing of the ion potassium.

* * * * *